United States Patent [19]

Bankit et al.

[11] Patent Number: 4,668,515

[45] Date of Patent: May 26, 1987

[54] METHOD AND COMPOSITIONS FOR SODIUM SELENITE ADMINISTRATION

[76] Inventors: Paul Bankit, 2587 Woodhill; Edward B. Crouse, 4920 Country Dr., both of Okemos, Mich. 48864

[21] Appl. No.: 733,618

[22] Filed: May 13, 1985

Related U.S. Application Data

[63] Continuation of Ser. No. 586,858, Mar. 6, 1984, abandoned.

[51] Int. Cl.$^4$ .............................................. A61K 33/04
[52] U.S. Cl. ..................................... 424/164; 424/162
[58] Field of Search ................................ 424/162, 164

[56] References Cited

U.S. PATENT DOCUMENTS 3,928,578 12/1975 Burns et al. ......................... 424/164
4,340,590 7/1982 Levitt ................................. 424/162

*Primary Examiner*—Stanley J. Friedman
*Attorney, Agent, or Firm*—Ian C. McLeod

[57] ABSTRACT

A method for the administration of sodium selenite as a mineral supplement in the diet as a flavored drink containing ascorbic acid and citric acid in novel compositions is described. The method and compositions are used to maintain the health of mammals particularly humans.

16 Claims, No Drawings

METHOD AND COMPOSITIONS FOR SODIUM SELENITE ADMINISTRATION

This application is a continuation of application Ser. No. 586,858, filed 3/6/84.

BACKGROUND OF THE INVENTION

(1) Field of the Invention

The present invention relates to a method and composition for the oral administration of sodium selenite to mammals, particularly humans. In particular the present invention relates to a flavored aqueous solution of sodium selenite containing edible acids, preferably citric and ascorbic acids in amounts which do not impair the effectiveness of the sodium selenite.

(2) Prior Art

Selenium compounds, both organic and inorganic, as mineral supplements with vitamins have been used for years to maintain good health. Recently it has been found that sodium selenite in dosages between about 200 and 300 micrograms per day is particularly effective in inhibiting the occurrence of tumors in healthy mammals (Selenium in Biology and Medicine, AVI Publishing Company, Inc., pages 98 to 102 (1981)). Essentially the compound is used in a prophylactic amount for this purpose.

Sodium selenite has been found to be inactivated by acids in a composition with a pH of less than about pH 2.75. The acidity of the composition plus the high acidity of the stomach of pH 1.2 to 1.5 retards the absorption of the sodium selenite into the blood stream. Ascorbic acid (Vitamin C) has been found to mask the affects of sodium selenite (Discovery of the Role of Selenium in Glutathione Peroxidase, AVI Publishing Company, page 10 (1981)).

The problem has been to formulate a palatable flavored fruit drink, particularly citrus flavored in the presence of citric acid and ascorbic acid, which are desirable flavor contributing ingredients, such that the drink has a pH of not less than about 2.75. A normal fruit drink has a pH of about 2.5 or less. Both ascorbic acid and citric acid are also regarded as being important for good health and are preferred.

Objects

It is therefore an object of the present invention to provide a flavored drink including sodium selenite and containing an edible acid particularly citric acid and ascorbic acid in amounts which do not impair the effectiveness of sodium selenite. Further it is an object of the present invention to provide a composition which is palatable. These and other objects will become increasinsly apparent by reference to the following description.

General Description

The present invention relates to a method for maintaining the health of a mammal with sodium selenite which comprises: orally feeding the mammal an effective amount of a flavored aqueous solution including sodium selenite admixed with an edible acid in an amount which retains the health maintaining effectiveness of the sodium selenite without the acid such that the health of the mammal is maintained.

Also the present invention relates to a sodium selenite composition for maintaining the health of a mammal which comprises in an aqueous solution: sodium selenite; an edible acid; and flavoring, wherein the composition contains between about 1 and $3 \times 10^{-4}$ percent by weight sodium selenite and between about 0.3 and 0.6 percent by weight acid, such that the pH is not less than pH 2.75.

In particular the present invention relates to a method for maintaining the health of a mammal with sodium selenite which comprises: orally feeding the mammal an effective amount of a flavored aqueous solution including sodium selenite admixed with citric and ascorbic acids in amounts which retain the health maintaining effectiveness of the sodium selenite without the acids such that the health of the mammal is maintained. Further the present invention relates to a sodium selenite composition for maintaining the health of a mammal which comprises in an aqueous solution: sodium selenite; citric acid and ascorbic acid; and flavoring, wherein the composition contains between about 1 and $3 \times 10^{-4}$ percent by weight sodium selenite and between about 0.3 and 0.6 percent by weight acid, such that the pH is not less than pH 2.75. The term "flavor" includes taste and olfactory sensation contributing ingredients such as flavor oils.

In particular the present invention relates to a mildly acidic, citrus flavored drink including sodium selenite and including (1) citrus pulpwash solids and citrus flavorings which provide significant amounts of ascorbic acid and (2) citric acid. The resulting composition is palatable and is useful for maintaining the health of the mammal, particularly humans.

SPECIFIC DESCRIPTION

Table 1 sets forth the formulation of a concentrate which is diluted with water (5 volumes of water to one volume of the solution) for administration to the mammal. The ingredients are shown in decreasing percents by volume. The principal ingredients are sodium selenite, citric acid, ascorbic acid and flavorings. In addition, citrus pulpwash, a source of small amounts of ascorbic acid, is included as well as various well known stabilizers or emulsifiers and shelf life extenders (spoilage inhibitors) such as potassium sorbate and sodium benzoate. The citric acid is added to achieve the desired pH in the diluted product taking into consideration the ascorbic acid present in the pulpwash solids and in the citrus concentrates. The concentrate can be stored and shipped without separation of the ingredients. The concentrate has a shelf life of at least three to four months when packaged in containers which do not allow transpiration of oxygen from the atmosphere.

TABLE 1

| | % Volume | | % Volume |
|---|---|---|---|
| Water | 14.510 | Heliotropine (Flavor) | 0.018 |
| Fructose aqueous solution 62° Brix | 54.600 | Gum Arabic (Stabilizer) | 0.018 |
| Orange Pulp Wash Solid (Includes ascorbic acid) | 9.460 | Benzaldehyde (Stabilizer) | 0.018 |
| Pineapple Concentrate (Flavor) | 9.460 | Lemon Oil 1X (Flavor) | 0.013 |
| Grapefruit Concentrate (Flavor, includes 10% by wt. ascorbic acid) | 4.730 | Vanillin (Flavor) | 0.013 |
| | | Ethyl Vanillin | 0.011 |
| | | Raspberry Juice Concentrate (Flavor) | 0.011 |
| *Citric Acid (Acid) (Tangy Flavor) | 2.270 | Ethyl Valerate (Stabilizer) | 0.009 |
| Passion Fruit Concentrate (Flavor) | 1.820 | Propylene Glycol (Stabilizer) | 0.011 |
| Lime Concentrate (Flavor, includes 10% | 1.820 | Aldehyde C-14 (Flavor) | 0.009 |
| | | Oenanthic Ether | 0.009 |

TABLE 1-continued

| | % Volume | | % Volume |
|---|---|---|---|
| by wt. ascorbic acid) | | (Flavor) | |
| *Sodium Benzoate (Shelf life extender) | 0.182 | Allyl Caproate (Flavor) | 0.009 |
| *Xanthan gum (Stabilizer) | 0.182 | California Orange Oil 1X (Flavor) | 0.009 |
| Sodium Selenite (1% by weight solution) | 0.150 | Ethyl Butyrate (Stabilizer) | 0.009 |
| Distilled Lime Oil (Flavor) | 0.064 | Potassium Sorbate (Shelf Life Extender) | 0.009 |
| Firmenich TM Apple #50.047/A (Flavor) | 0.064 | Grapefruit Oil 5Z (Flavor) | 0.009 |
| Ketone 18 (Flavor) | 0.055 | Florida Orange Oil 5X (Flavor) | 0.009 |
| Amyl Butyrate (Flavor) | 0.051 | Aldehyde C-22 (Flavor) | 0.006 |
| Linalyl Formate (Stabilizer for oils) | 0.046 | Oil of Bitter Almond (Flavor) | 0.004 |
| Grapefruit Oil 1X (Flavor) | 0.036 | Imitation Rose Oil (Flavor) | 0.006 |
| Grenadine Aldehyde (Flavor) | 0.027 | Genuine Oil of Cognac (Flavor) | 0.004 |
| Aldehyde C-18 (Flavor) | 0.027 | F D & C Red #40 (Coloring) | 0.004 |
| Ester Gum 8 B.G. (Stabilizer) | 0.027 | Firmenich TM Orange Oil #59.432/T (Flavor) | 0.002 |
| Imitation Neroli oil (Flavor) | 0.027 | Aldehyde C-19 (Flavor) | 0.002 |
| Amyl Valerate (Flavor) | 0.027 | Amyl Acetate (Stabilizer) | 0.002 |
| Citral (Flavor) | 0.027 | Ethyl Vanillin (Flavor) | 0.002 |
| Florida Orange Oil 1X (Flavor) | 0.026 | | |
| Paramethyl Benzyl Anthranilite (Stabilizer) | 0.024 | | 100.00% |
| Ethyl Alcohol (Flavor) | 0.022 | | |
| Ethyl Acetate (Flavor) | 0.020 | | |
| Orange Terpenes (Flavor) | 0.018 | | |

*As solids by Bulk Volume

Table 2 shows the percent by weight of the principal ingredients in the (5:1) final product which is the diluted concentrate (5:1).

TABLE 2

| | % by Weight |
|---|---|
| Water and sweetener | about 90 to 95 |
| Sodium selenite | $1$ to $3 \times 10^{-4}$ |
| Pulp Wash Solids | about 1 to 2 |
| Citric Acid | 0.3 to 0.6 |
| Citric Concentrates | 1.5 to 2.5 |
| Flavorings | 2 to 5 |
| Stabilizers and Preservatives | 0.1 to 0.2 |

The fruit drink was prepared using conventional mixing techniques. The ingredients which form the smallest proportions of the mix were combined. Assuming a total of 100 gallons (378.5 liters) is being prepared, those ingredients forming less than 0.064 percent by volume were combined with sodium benzoate, sodium selenite and xanthan gum and then in turn combined in a blending tank with water, pulp wash solids, pineapple concentrate, grapefruit concentrate, citric acid, passion fruit concentrate, and lime concentrate. The resulting mixture was then combined at room temperature with warm (55° F. (12.8° C.) or warmer) fructose solution.

The concentrated mixture was combined with 500 gallons (1892.5 liters) of water to produce the diluted concentrate as final product for administration. The water was tested to make certain there is no selenium as an impurity. This prevents the accidental inclusion of more than the desired amount of selenium in the final product.

Six gallons of the final product is used to prepare 192 servings of 4 oz each in automatic bottling machinery. Six (6) gallons of the diluted concentrate weighs 23,838.5 grams and thus has a density of about 1.05 gm/cc. The sodium selenite is preferably present in an amount of 8 mg per gallon which calculates to $2 \times 10^{-4}$ percent and is preferably included in an amount between 1 and $3 \times 10^{-4}$ percent. The citric acid and ascorbic acid combined are present in an amount of 103.2 grams per gallon of diluted concentrate. This calculates to 2.59 percent by weight of the acids. The lime and grapefruit concentrates are the principal sources of ascorbic acid. The pulp wash consitutes between about 1 and 2 percent by volume of the diluted concentrate. When diluted, the solution requires refrigeration below 5° C. (41° F.) and above freezing if stored for periods longer than 15 days unless packaged in non-permeable containers. The product is served in single-use, non-permeable packages which do not require refrigeration after opening.

The diluted concentrate is designed to deliver between about 200 to 300 micrograms of sodium selenite per four ounce (118 cc) serving as a daily dosage unit and has a pH between about pH 2.75 and pH 3.25. The dilute composition contains between about 1.8 to 2.5 micrograms per ml of sodium selenite and between about 0.3 and 0.6 percent by weight of citric and ascorbic acids.

The dilute composition was tested in animals and found to be non-toxic in mice and rabbits. The formation of spontaneous mammory tumors was inhibited in C3H mice. The composition has been taken by human volunteers without ill effect.

Other edible acids, such as lactic acid, phosphoric acid and acetic acid might be used for flavoring in the method and compositions of the present invention. Citric acid is preferred.

We claim:

1. A method of feeding a mammal sodium selenite to provide the mammal with a daily dosage of selenium which comprises:
   orally feeding the mammal an effective amount of a flavored aqueous solution which comprises sodium selenite admixed with citric and ascorbic acids in amounts which produce a pH of not less than about 2.75 wherein the ascorbic acid is provided by citric concentrate in an amount between 1.5 and 2.5 percent by weight in the solution, wherein the citric acid is between about 0.3 and 0.6 percent by weight of the solution, wherein the solution contains between about 1 and $3 \times 10^{-4}$ percent by weight sodium selenite, wherein the solution can be stored and shipped without separation of ingredients and wherein the aqueous flavored solution is as effective in providing a daily dosage of selenium as a solution of the sodium selenite without the acids.

2. The method of claim 1 wherein the solution is fed to the mammal daily in a dosage unit form containing between about 1.8 to 2.5 micrograms per ml of sodium selenite.

3. The method of claim 2 wherein the dosage unit form is about 118 ml providing about 200 to 300 micrograms daily.

4. The method of claim 2 wherein the mammal is a human.

5. The method of claim 1 wherein the flavoring is derived from citrus concentrates and oils and wherein the solution contains washed orange pulp in an amount between about 1 and 2 percent by volume.

6. A sodium selenite composition for feeding to a mammal to provide a daily dosage of selenium which comprises in an aqueous solution:
   (a) sodium selenite;
   (b) citric acid and ascorbic acid; and
   (c) flavoring, wherein the composition contains between about 1 and $3 \times 10^{-4}$ percent by weight sodium selenite and acid in an amount such that the pH is not less than pH 2.75 wherein the ascorbic acid is from citric concentrates in an amount between 1.5 and 2.5 percent by weight of the solution, wherein the citric acid is between about 0.3 and 0.6 percent by weight of the solution, wherein the solution can be stored and shipped without separation of ingredients.

7. The composition of claim 6 wherein the flavoring is derived from citrus oils and wherein the composition contains washed orange pulp in an amount between about 1 and 2 percent by volume.

8. The composition of claim 7 containing about $2 \times 10^{-4}$ percent by weight of the sodium selenite and about 2.59 percent by weight acid.

9. The composition of claim 7 wherein the composition includes emulsifiers to maintain the citrus oils in solution, a coloring agent and fructose.

10. A sodium selenite concentrate composition adapted to be diluted with water in a ratio of 1 part concentrate to 5 parts water to provide a dilute composition for feeding to a mammal to provide its daily dosage of selenium which comprises in an aqueous solution:
    (a) sodium selenite;
    (b) citric acid and ascorbic acid;
    (c) flavoring; and
    (d) shelf life extenders which prevent spoilage, wherein the concentrate when diluted contains between about 1 and $3 \times 10^{-4}$ percent by weight sodium selenite and between about 0.3 and 0.6 percent by weight acid in an amount such that the pH is not less than pH 2.75 wherein the ascorbic acid acid is provided by citric concentrate in an amount between 1.5 and 2.5 percent by weight of the solution, wherein the citric acid is between about 0.3 and 0.6 percent by weight of the solution, wherein the solution can be stored and shipped without separation of ingredients.

11. The concentrate composition of claim 10 including citrus pulp wash solids in an amount between about 8 and 11 percent by volume.

12. The concentrate composition of claim 10 wherein the ascorbic acid is present in a citrus concentrate.

13. A method for feeding a mammal sodium selenite to provide the mammal with a daily dosage of selenium which comprises:
    orally feeding the mammal an effective amount of a flavored aqueous solution which comprises sodium selenite admixed with an edible acid selected from lactic acid, phosphoric acid, citric acid and acetic acid including ascorbic acid used in fruit drinks for flavor in an amount which produces a pH of not less than about 2.75, wherein the ascorbic acid is provided by citric concentrate in an amount between 1.5 and 2.5 percent by weight of the solution, wherein the edible acid is between about 0.3 and 0.6 percent by weight of the solution, wherein the solution contains between about 1 and $3 \times 10^{-4}$ percent by weight sodium selenite wherein the solution can be stored and shipped without separation of ingredients, and wherein the aqueous flavored solution is as effective as a solution of the sodium selenite without the acid.

14. The method of claim 13 wherein the edible acid includes ascorbic acid and another edible acid for flavor.

15. A sodium selenite composition for feeding to a mammal to provide a daily dosage of selenium which comprises in an aqueous solution:
    (a) sodium selenite;
    (b) an edible acid including ascorbic acid; and
    (c) flavoring, wherein the composition contains between about 1 and $3 \times 10^{-4}$ percent by weight sodium selenite and acid in an amount such that the pH is not less than pH 2.75 wherein ascorbic acid is provided by citric concentrate in an amount between 1.5 and 2.5 percent by weight of the solution, wherein the edible acid is between about 0.3 and 0.6 percent by weight of the solution, wherein the solution can be stored and shipped without separation of ingredients.

16. The composition of claim 15 wherein the edible acid includes ascorbic acid and another edible acid for flavor.

* * * * *